US011554386B2

(12) United States Patent
Pernot et al.

(10) Patent No.: US 11,554,386 B2
(45) Date of Patent: Jan. 17, 2023

(54) ULTRASOUND IMAGING AND THERAPY DEVICE

(71) Applicants: CARDIAWAVE, Paris (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR)

(72) Inventors: Mathieu Pernot, Paris (FR); Michael Vion, La Chaussée Saint Victor (FR); Mickael Tanter, Bagneux (FR)

(73) Assignees: CARDIAWAVE, Paris (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 924 days.

(21) Appl. No.: 16/095,304

(22) PCT Filed: Apr. 21, 2017

(86) PCT No.: PCT/EP2017/059556
§ 371 (c)(1),
(2) Date: Oct. 19, 2018

(87) PCT Pub. No.: WO2017/182655
PCT Pub. Date: Oct. 26, 2017

(65) Prior Publication Data
US 2019/0126317 A1 May 2, 2019

(30) Foreign Application Priority Data

Apr. 22, 2016 (EP) .................................. 16305472

(51) Int. Cl.
A61B 8/00 (2006.01)
B06B 1/06 (2006.01)
(Continued)

(52) U.S. Cl.
CPC .......... B06B 1/0625 (2013.01); A61B 8/0833 (2013.01); A61B 8/429 (2013.01);
(Continued)

(58) Field of Classification Search
CPC ..... A61B 17/225; A61B 17/2258; A61B 8/08; A61B 8/0833; A61B 8/085; A61B 8/429;
(Continued)

(56) References Cited

U.S. PATENT DOCUMENTS 5,095,908 A * 3/1992 Belikan .............. A61B 17/2258
600/439
5,520,188 A 5/1996 Hennige et al.
(Continued)

FOREIGN PATENT DOCUMENTS

CN 101553173 10/2009
CN 202198617 4/2012
(Continued)

OTHER PUBLICATIONS

Canney et al., "Acoustic characterization of high intensity focused ultrasound fields: A combined measurement and modeling approach", JASA 2008 (Year: 2008).*
(Continued)

Primary Examiner — Christopher L Cook
(74) Attorney, Agent, or Firm — BakerHostetler

(57) ABSTRACT

An ultrasound imaging and therapy device includes an array of concentric annular ultrasound transducers, and an ultrasound imaging device situated inside an innermost transducer of the plurality of concentric annular ultrasound transducers, wherein it further comprises a mechanical link-
(Continued)

Figure 1:
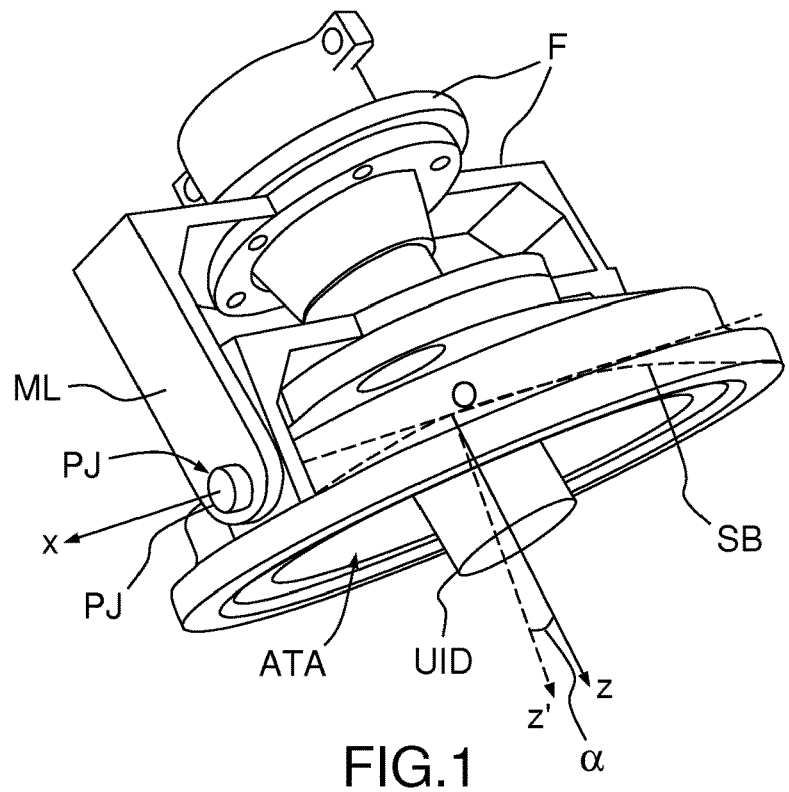

age allowing a tilting movement of the array of concentric annular ultrasound transducers with respect to the ultrasound imaging device and in that the ultrasound imaging device protrudes in an axial direction from the array of concentric annular ultrasound transducers; whereby the ultrasound imaging device can be kept stationary and in direct or indirect contact with a patient's skin while the array of concentric annular ultrasound transducers is tilted so as to move a focal point of ultrasound waves generated by the concentric annular ultrasound transducers within an imaging region of the ultrasound imaging device.

15 Claims, 3 Drawing Sheets

(51) Int. Cl.
| | | |
|---|---|---|
| *A61N 7/00* | (2006.01) | |
| *G10K 11/00* | (2006.01) | |
| *A61B 17/225* | (2006.01) | |
| *G10K 11/35* | (2006.01) | |
| *A61B 8/08* | (2006.01) | |
| *G10K 11/34* | (2006.01) | |

(52) U.S. Cl.
CPC .......... *A61B 8/4461* (2013.01); *A61B 8/4483* (2013.01); *A61B 17/225* (2013.01); *A61B 17/2258* (2013.01); *A61N 7/00* (2013.01); *G10K 11/004* (2013.01); *G10K 11/34* (2013.01); *G10K 11/355* (2013.01); *A61B 8/08* (2013.01); *A61B 8/085* (2013.01); *A61N 2007/0004* (2013.01); *A61N 2007/0052* (2013.01); *A61N 2007/0082* (2013.01); *A61N 2007/0086* (2013.01)

(58) Field of Classification Search
CPC ................ A61B 8/4461; A61B 8/4483; A61N 2007/0004; A61N 2007/0052; A61N 2007/0082; A61N 2007/0086; A61N 7/00; B06B 1/0625; G10K 11/004; G10K 11/34; G10K 11/355
See application file for complete search history.

(56) References Cited

U.S. PATENT DOCUMENTS

| | | | |
|---|---|---|---|
| 5,524,625 A | 6/1996 | Okazaki et al. | |
| 2009/0230822 A1 | 9/2009 | Kushculey et al. | |
| 2011/0118598 A1* | 5/2011 | Gertner ................... | A61N 7/00 600/431 |
| 2012/0046592 A1 | 2/2012 | Albright et al. | |
| 2014/0107536 A1 | 4/2014 | Murakami | |
| 2016/0317844 A1* | 11/2016 | Lupotti ................. | A61N 7/022 |

FOREIGN PATENT DOCUMENTS

| | | |
|---|---|---|
| JP | 5-309099 A | 11/1993 |
| JP | 6-105851 A | 4/1994 |
| JP | 11-164837 A | 6/1999 |
| JP | 2013-000269 A | 1/2013 |
| JP | 2013-534176 A | 9/2013 |
| WO | 2012/024545 A2 | 5/2012 |

OTHER PUBLICATIONS

Miller, et al., "Histotripsy Cardiac Therapy System Integrated with Real-time Motion Correction", Ultrasound Med Biol., vol. 39, No. 12, pp. 2362-2373, Dec. 2013.
Arnal, et al., "Tunable time-reversal cavity for high-pressure ultrasonic pulses generation: A tradeoff between transmission and time compression", Appl. Phys. Lett., 101, 064104, 2012.
Arnal, et al., "In vivo real-time cavitation imaging in moving organs", Phys Med Biol., vol. 62, No. 3, pp. 843-857, Feb. 7, 2017.
Wang, et al., "Quantitative ultrasound backscatter for pulsed cavitational ultrasound therapy—histotripsy", IEEE Trans Ultrason Ferroelectr Freq Control., vol. 56(5), pp. 995-1005, May 2009.
Xu, et al., "Noninvasive creation of an atrial septal defect by histotripsy in a canine model", Circulation, vol. 121, No. 6, pp. 742-749, Feb. 16, 2010.
Pernot, et al., "3-D real-time motion correction in high-intensity focused ultrasound therapy", Ultrasound Med Biol., 30(9), pp. 1239-1249, Sep. 2004.
Arnal, "Elastographie pour le suivi des thérapies par ultrasons focalisés et nouveau concept de cavitéà retournement temporel pour l'histotripsie" ("Elastography for monitoring focused ultrasound therapy and new concept of time-reversal cavity for histotripsy"), University of Paris VII, Jan. 17, 2013.
English translation of Notice of Rejection issued in Japanese Patent Application No. 2018-555162 dated Dec. 22, 2020.
First Office Action in CN Application No. 201780024987.2, dated Aug. 31, 2022.

* cited by examiner

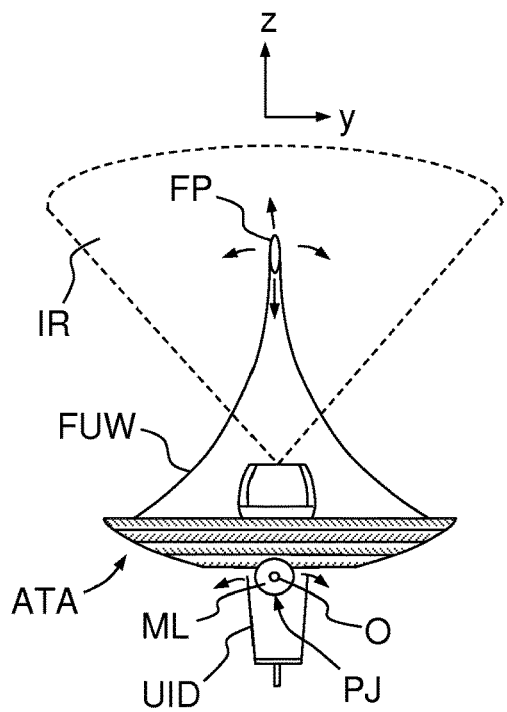 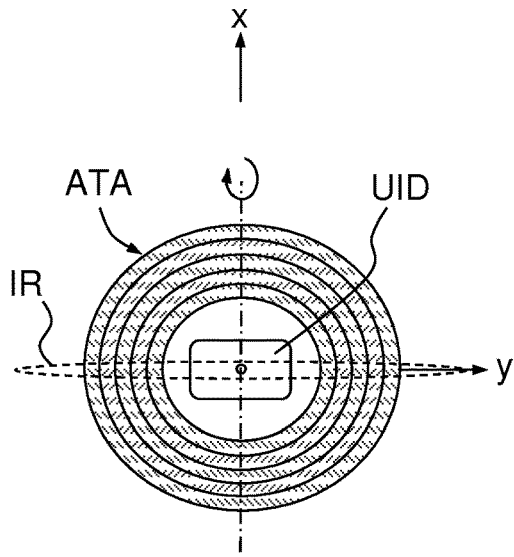
FIG.4A　　　　　　FIG.4B
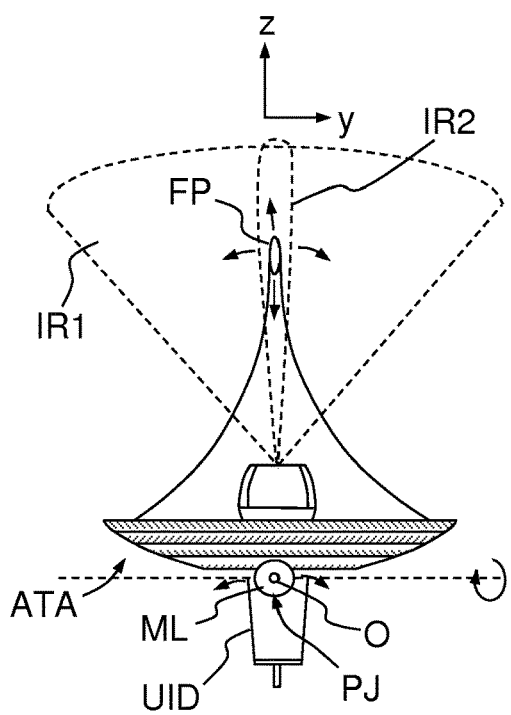 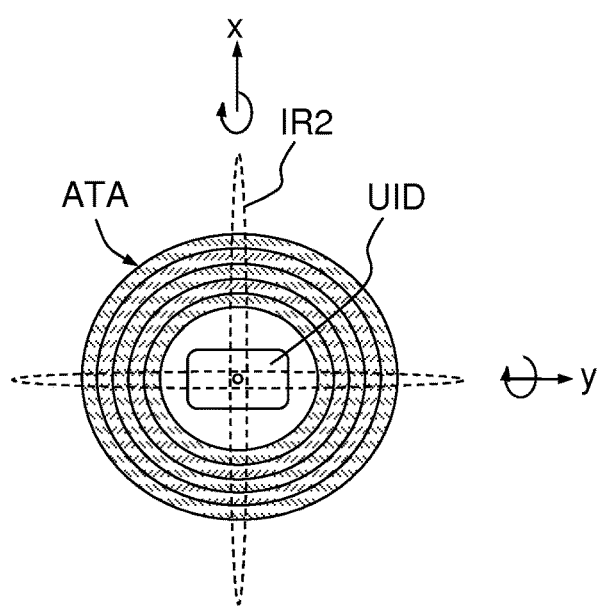
FIG.5A　　　　　　FIG.5B

ULTRASOUND IMAGING AND THERAPY DEVICE

CROSS-REFERENCE TO RELATED APPLICATIONS

This application is a National Stage of International patent application PCT/EP2017/059556, filed on Apr. 21, 2017, which claims priority to foreign European patent application No. 16305472.9, filed on Apr. 22, 2016, the disclosures of which are incorporated by reference in their entirety.

The invention relates to an ultrasound imaging and therapy device, in particular for cardiac therapy over a beating heart, and more particularly for performing non-invasive cardiac treatments e.g. by lithotripsy, histotripsy, shock waves, HIFU (High Intensity Focused Ultrasound) or ultrasonic drug delivery.

Ultrasounds are used as a therapeutic tool for several diverse applications: dental hygiene, fragmentation of kidney stones (lithotripsy), ablation of tumors, etc. Recently, applications to cardiac surgery have also been suggested (myocardial ischemia by myocardial revascularization, refractory angina pectoris, hypertension by renal denervation or vascular calcification). These applications are based on lithotripsy or histotripsy (mechanical fracturing of calcifications/kidney stones or tissues, respectively, by ultrasonic shock waves) or HIFU (wherein high intensity ultrasounds waves induce local heating of tissues). Other therapeutic applications of ultrasounds include sonoporation, wherein lower-intensity focused ultrasound wave allow localized drug delivery.

In order to target and treat a volume of tissue within the body, the focal point of the therapeutic ultrasonic waves must be moved along one, two or preferably three dimensions. This is accomplished in prior art by moving the transducer, both along a plane parallel to the surface of the body, as well as towards and away from the body. This cannot be done over a beating heart as it is required to visualize and track continuously and in real-time the heart and its motions with an imaging device, and to correct the position of the focal point of the therapeutic ultrasound waves in a three-dimensional referential in order to remain locked on the targeted region both for safety and efficacy concerns.

Document US 2012/0046592 discloses an ultrasound imaging and therapy device comprising a concave HIFU transducer, at the center of which is situated an imaging transducer; the resulting assembly is enclosed in a liquid-filled housing, closed by a flexible membrane. The focal point of the therapeutic ultrasound waves is steered laterally by tilting the HIFU transducer —but not the imaging transducer—and longitudinally by translating the HIFU transducer together with the imaging transducer.

Using ultrasounds for treating a beating heart is challenging as the real-time image-guiding and tracking must be performed with a high degree of accuracy to avoid potentially fatal injuries induced by misguided ultrasound waves, despite the fact that the heart is in constant motion. Such real-time accuracy requirements are particularly difficult to meet in non-invasive applications, wherein ultrasounds are applied transthoracically; more invasive (e.g. transesophageal) approaches are simpler to implement but have obvious drawbacks, such as the limited spacing available or the potential damage of the esophagus.

The paper by R. M. Miller et al. "Histotripsy cardiac therapy system integrated with real-time motion correction", Ultrasound in Med. & Biol. Vol. 39, No. 12, pp. 2362-2373 (2013) discloses a histotripsy-based transthoracic cardiac therapy system integrated with real-time motion correction, allowing to follow the movement of a target region of a beating heart to be treated. This system is based on a therapy device comprising a plurality of concentric annular ultrasound transducers, with a sonography probe at its center (for a similar device, see U.S. Pat. No. 5,520,188). By feeding the annular transducers with electric driving signals having an appropriate phase (and, optionally, intensity) relationship, it is possible to generate focused ultrasound waves, and to steer the focal point in an axial direction but not to cover a large treatment region (surface or volume) and to spread the therapeutic waves over a precisely controlled region; the sonography probe allows monitoring the treatment. In real world application, however, lateral steering of the focal point is required too. Simply translating the therapy device would be unsatisfactory, at least in trans-thoracic application, where the sonography probe has to be very precisely placed between two ribs to acquire in real-time good quality images for guiding, targeting and monitoring the treatment, and therefore requires to be kept stationary and in direct or indirect (e.g. mediated by a thin layer, typically less than 5 mm thick, of a ultrasound-conducting medium) contact with the patient's skin during the application of therapeutic ultrasounds.

R. M. Miller and coworkers suggest using a two-dimensional ultrasound phased array to perform three-dimensional electronics steering of the focal point of the ultrasound waves. This approach would be extremely complex to implement, requiring tens or hundreds of precisely phased driving signals, directed to respective ultrasound transducers. A suitable electronics driver is not commercially available and would be extremely expensive to develop.

In his PhD thesis "*Elastographie pour le suivi des thérapies par ultrasons focalisés et nouveau concept de cavité à retournement temporel pour l'histotripsie*" ("Elastography for monitoring focused ultrasound therapy and new concept of time-reversal cavity for histotripsy"), University of Paris VII, Jan. 17, 2013, Bastien Arnal suggests using a time-reversal cavity to perform three-dimensional electronic steering of focused ultrasound waves for cutting mitral chords. A time-reversal cavity suitable for histotripsy therapy is also described in the paper by B. Arnal et al. "Tunable time-reversal cavity for high-pressure ultrasonic pulses generation: A tradeoff between transmission and time compression", Applied Physics Letters 101, 064104 (2012). Again, this approach is very difficult to implement and requires sophisticated electronics.

Much simpler devices, based on a single, concave ultrasound transceiver carrying at its center a sonography probe have been used in experimental setups, but are not suitable for real-life applications as it would be impossible to steer the focal point of the ultrasound waves by mechanically steering the therapeutic probe while simultaneously keeping the sonography imaging probe stationary and in direct or indirect contact with the patient's skin. More particularly, it would be impossible to change the focal depth of the therapeutic ultrasound waves without moving the sonography imaging probe towards or away from the body, and at a position allowing continuous and real-time acquisition of good-quality images and tracking of a living organ such as a beating heart. Moving the sonography imaging probe towards or away from the body would immediately result in a strong degradation of the imaging quality as non invasive echocardiography requires a mandatory positioning of the sonography imaging probe in the intercostal space in contact with the skin.

The invention aims at overcoming these drawbacks of the prior art. More precisely, it aims at providing an imaging and therapy device allowing two- or three-dimensional steering of focused ultrasound waves under real-time guidance and monitoring from an ultrasonic imaging device (e.g. a sonography probe), while avoiding excessive complexity, cost and image degradation of the ultrasonic guidance.

An object of the present invention, allowing to achieve this aim, is an ultrasound imaging and therapy device comprising an array of concentric annular ultrasound transducers, for the generation of therapeutic focused waves, and an ultrasound imaging device situated inside an innermost transducer of said plurality of concentric annular ultrasound transducers, characterized in that it further comprises a mechanical linkage allowing a tilting movement of the array of concentric annular ultrasound transducers with respect to the ultrasound imaging device; whereby the ultrasound imaging device can be kept stationary and in direct or indirect contact with a patient's skin while the array of concentric annular ultrasound transducers is tilted so as to move a focal point of ultrasound waves generated by the concentric annular ultrasound transducers within an imaging region of said ultrasound imaging device. Importantly, the ultrasound imaging device protrudes in an axial direction from the array of concentric annular ultrasound transducers (more particularly, it extends beyond the foremost point of the array, in propagation direction of the ultrasounds, even when the latter is tilted). This is instrumental for allowing the ultrasound imaging device to remain in direct or indirect contact with the patient's skin during the treatment. For instance; the ultrasound imaging device may protrude from the array of concentric annular ultrasound transducers by a length comprised between 10 and 100 mm, preferably between 10 and 50 mm and even more preferably between 10 and 24 mm. The actual value depends on the outer diameter of the outermost annular transducer and of the required tilt amplitude. For instance, considering an outmost transducer having a diameter of 55 mm, the ultrasound imaging device should protrude by at least 10 mm to allow a tilting of ±10° when the device is applied to a flat surface.

The inventive device uses a hybrid combination of electronics and mechanical steering. Axial steering is performed electronically and enables to move the focal point to multiple depths, as in the previously-cited paper by R. M. Miller et al.; lateral steering is performed mechanically, by tilting the ultrasound transducer without moving the imaging device. The combination of electronic axial steering and mechanical lateral steering allows moving the focal point of the ultrasound waves in two or three dimensions. As explained above, this is not achieved at the expense of image quality thanks to the electronic axial steering of the focal point and to the protruding imaging device.

Particular embodiments of such a therapy device constitute the subject-matter of the dependent claims.

Figure 2:
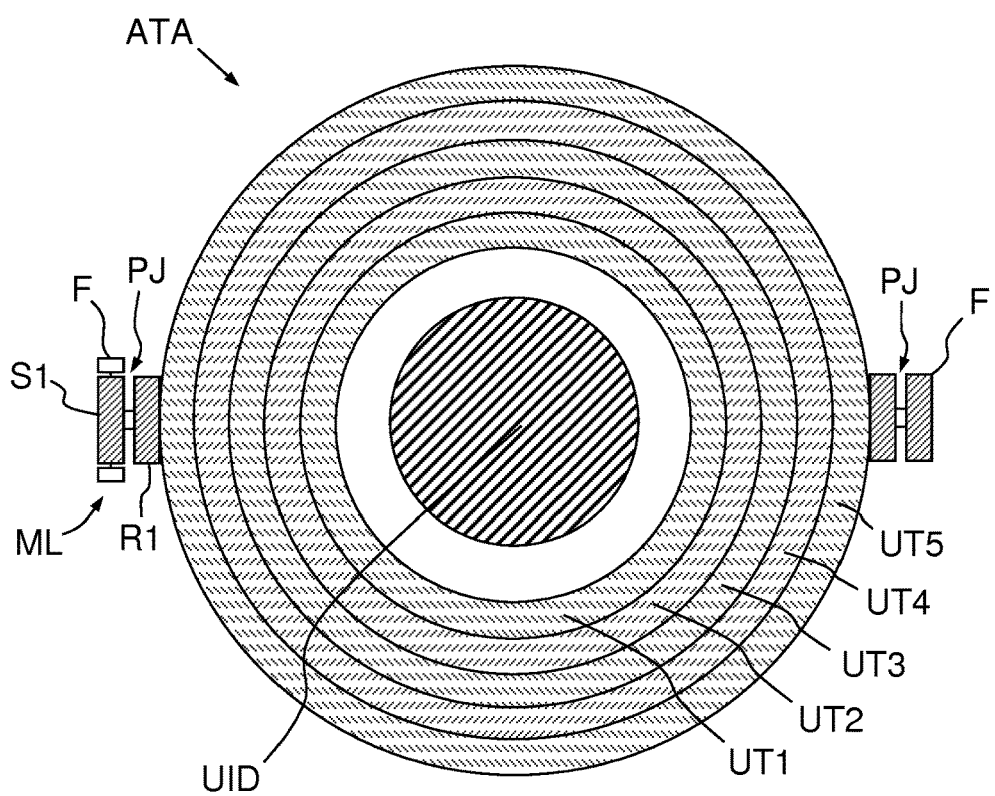
Figure 3:
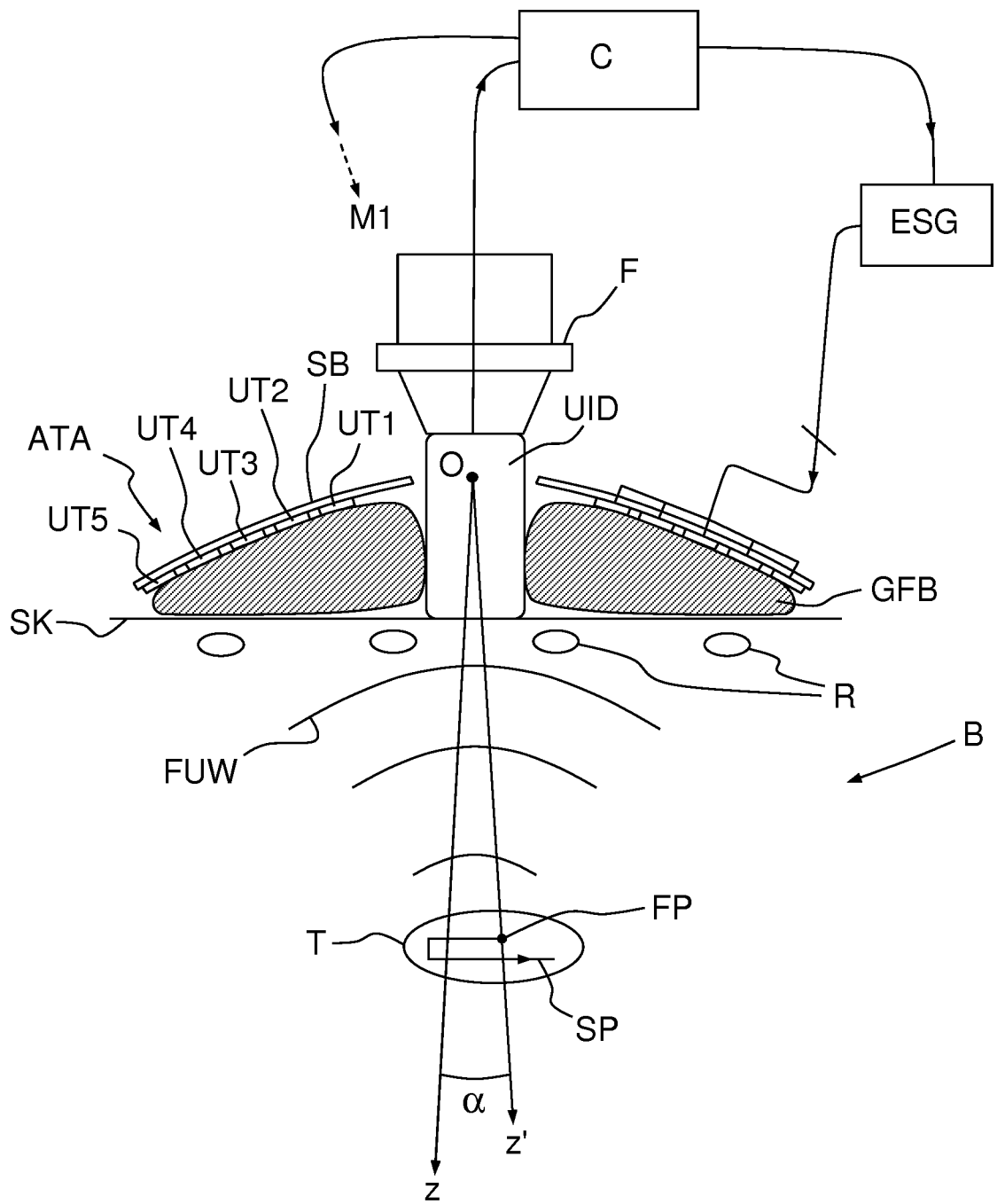

Additional features and advantages of the present invention will become apparent from the subsequent description, taken in conjunction with the accompanying drawings, which show:

FIG. 1, a simplified lateral view of an imaging and therapy device according to an embodiment of the invention;

FIG. 2, a bottom view of the device of FIG. 1;

FIG. 3, a sectional view of the device of FIG. 1, seen in operational conditions;

FIGS. 4A and 4B, a schematic representation of two-dimensional steering monitored by single-plane imaging; and FIGS. 5A and 5B, a schematic representation of three-dimensional steering monitored by bi-plane imaging.

The drawings are not to scale.

An imaging and therapy device according to an embodiment of the invention, illustrated on FIGS. 1, 2 and 3, comprises an array ATA of annular ultrasound transducers UT1-UT5 of increasing radii, disposed concentrically and aligned on a spherical bowl SB. According to different embodiments, not illustrated on the figures, the transducers may be arranged on a concave but non-spherical (e.g. parabolic) bowl, or even be arranged in a plane. Such an array of transducers is described e.g. by the above-referenced document U.S. Pat. No. 5,520,188.

Five transducers are represented on FIGS. 2 and 3, but a different number may be used, e.g. up to a few tens; a number comprised between 5 and 20 is preferred to avoid excessive complexity. Annular transducers are preferably circular, as represented on FIG. 2; more exactly, each annular transducer may have the shape of a right conical frustum with circular basis. Other shapes are also possible (e.g. elliptical, rectangular . . . ). They may be continuous or formed by discrete segments.

As in U.S. Pat. No. 5,520,188 and in the above-referenced paper by R. M. Miller et al., an ultrasound imaging device UID—e.g. a bi-dimensional, bi-plane or three-dimensional sonography probe—is situated at the center of the array ATA, inside the innermost transducer UT1.

Unlike in the prior art, however, the imaging device is not directly affixed to the transducer array ATA, but is connected to it through a mechanical linkage ML, a possible structure thereof is illustrated on FIGS. 1 and 2. The mechanical linkage ML allows tilting the transducer array ATA with respect to the imaging device UID, i.e. rotating it around at least an axis Ox, perpendicular to the viewing axis Oz of the imaging device UID. According to a different embodiment of the invention, the mechanical linkage ML allows rotating the transducer array ATA around two axes Ox, Oy mutually perpendicular and perpendicular to the viewing axis Oz. Preferably, the pivot point O corresponds to the center of the concave bowl of the transducer array ATA.

An electrical motor M1 (only represented on FIG. 2) actuates the rotational degree of freedom of the linkage ML. In a two degree of freedom embodiment, two independent motors are usually provided.

In the embodiment of FIGS. 1-3, mechanical linkage ML is based on a pivot joint. More precisely, it comprises:
  a fixed frame F, to which the imaging device UID is fixedly connected; and
  a pivot joint PJ of axis Ox, actuated by motor M1, comprising a stator S1 fixedly connected to the frame F and a rotor R1 fixedly connected to the transducer array.

In a two-degree of freedom embodiment, linkage ML may include a universal joint, comprising two pivot joints having perpendicular axes and connected in series, or even a ball joint which provides an additional, usually unnecessary, rotational degree of freedom around the z axis.

On FIGS. 1 and 3 it can be seen that the normal axis Oz' to the transducer array is inclined by an angle α with respect to the imaging axis Oz of the imaging device, the latter being kept substantially perpendicular to the skin SK of the body B of a patient. Ultrasound waves FUW emitted by the ultrasound transducers UT1-UT5 are focused at a focal point FP lying on the z' axis. The spherical (more generally, concave) shape of the transducer array ensures the focusing of ultrasound at a "geometrical" or "natural" focal length. Electronics focusing, obtained by introducing suitable delays between the signals feeding the transducers, enables to move the focal point to multiple depths.

The focal point FP can then be steered electronically, by changing the relative phase of the driving signals of the ultrasound transducers, in the Oz' direction and mechanically, by tilting the transducer array, in a direction or plane perpendicular to Oz (actually, on a circular segment or spherical surface which can be approximated by a straight line, or a plane, for a small tilting angle α). This way, the focal point FP can be steered along a two- or three-dimensional path SP within a target region T of the body B, under constant monitoring from the imaging device UID, which does not move. In the example of FIG. 1, the imaging device UID is positioned between two adjacent ribs R, which allows acquiring high-quality images of the target region T.

It is interesting to note that a small tilting angle α is sufficient for most application. For instance, if the ultrasound waves FUW are focused at a depth of 5 cm below the patient's skin, a tilting of less than ±6° is sufficient to scan a 1 cm wide target region. According to different embodiments of the invention, the mechanical linkage ML may be suitable for allowing a tilting or ±10°, or even of ±20°.

While the imaging device UID is kept stationary and in direct or indirect contact with the patient's skin (actually, even "direct" contact usually implies the interposition of a thin layer of sonography gel), the ultrasound transducers UT1-UT5 cannot, as the ultrasound imaging device protrudes from array in order to provide free space to enable its tilting. A deformable gel-filled or degassed water-filled bag GFB—possibly with a hole in its center, in register to the imaging device UID—may be interposed between the transducer array ATA and the patient's skin to allow propagation of the focused ultrasound waves.

On FIG. 3, reference ESG designates an electronic signal generator, generating individual driving signals for the ultrasound transducers of the array ATA. The signals are generated with a variable phase shift, which determines the axial position (i.e. the position along the Oz' axis) of the focal point FP. A controller C—e.g. a suitably-programmed computer or microcontroller—drives the electronic signal generator ESG and the motor M1 (or the two motors in a two-degree of freedom embodiment) actuating the linkage ML in order to steer the focal point FP. The controller may receive image data from the imaging device UID in order to perform the steering automatically. For example, the controller C may drive the electronic signal generator ESG and the motor M1 so that the focal point FP scans a target region T of a heart following a predetermined path SP while simultaneously compensating the physiological movements of the target. Suitable motion compensation algorithms are described in the previously-cited paper by R. M. Miller et al. and in M. Pernot et al. "3-D real-time motion correction in high-intensity focused ultrasound therapy" Ultrasound in Med Biol 2004, 30, 9, 1239-1249.

Advantageously, the controller may be configured to stop the treatment immediately if the image data from the imaging device indicate that the focal point has moved outside the target region, thus reducing the risk of inflicting lesions to the hearth tissues.

In some embodiments, the controller may also be configured for processing the image data received from the imaging device for extracting therefrom information related to the treatment, e.g. a cavitation activity indicator. This information may then be used to automatically adapt the intensity level of the focused ultrasound waves. The paper by B. Arnal et al. "In vivo real-time cavitation imaging in moving organs", Physics in Medicine & Biology 62, 843-857 (2017) describes a method for imaging cavitation bubbles generated by focused ultrasound waves emitted by a concave ultrasound transducer accommodating, at its center, an ultrasound imaging device. According to this method, the ultrasound imaging devices emits a sequence of imaging pulses and acquires the corresponding echoes between two successive cavitation-inducing pulses. The echoes are then processed to extract images of the cavitation bubbles, which are distinguished from the surrounding tissues. If no cavitation bubble is detected, the controller may deduce that the ultrasound power is insufficient, and increase it (preferably under the control of a human operator). If cavitation bubbles are detected closer to the transducer than the expected focal point, the controller may deduce that the ultrasound power is excessive, and reduce it.

In an exemplary embodiment of the invention, the imaging and therapy device comprises 12 annular ultrasound transducer arranged on a spherical bowl, whose radii are listed in Table 1 below:

TABLE 1

| Element # | Outer radius in millimeter |
|---|---|
| 1 | 27.05 |
| 2 | 30.50 |
| 3 | 33.61 |
| 4 | 36.52 |
| 5 | 39.25 |
| 6 | 41.82 |
| 7 | 44.26 |
| 8 | 46.58 |
| 9 | 48.81 |
| 10 | 50.95 |
| 11 | 53.00 |
| 12 | 55.00 |

Such an array has a "natural" focal length of 110 mm (corresponding to the radius of the spherical bowl SB), that may be electronically adjusted between 40 and 180 mm. It has been found that a fixed imaging transducer in contact with the patient allows a transducer tilt of ±20° with limited loss due to the fixed imaging transducer. The combination of the focal depth and tilt value allows such transducer array to move laterally the focal point by ±66 mm. In using such a transducer array for therapy, with a two-degree of freedom linking, the focal point may be swept through a volume of more than 810 cubic centimeters without displacement the imaging transducer from the patient. In this embodiment, a stepper motor is mounted directly on each of the two axes of rotation (Ox, Oy) to mechanically tilt the transducer array. Such stepper motors with 200 steps driven at 200 Hz allow moving mechanically the focal point at a speed ranging from 0.3 to 20 millimeter per millisecond.

FIGS. 4A and 4B illustrates an embodiment wherein the ultrasound imaging device UID is a two-dimensional sonography probe defining an imaging region IR which is substantially planar and lies in the yz plane (imaging plane). The array of ultrasound transducers ATA is mounted so as to be rotatable around axis Ox. Electronic steering along the Oz axis and tilting of the array ATA around the Ox axis allow displacing the focal point FP (which is actually a region of finite volume and with an elongate shape along Oz') within the planar imaging region IR.

FIGS. 5A and 5B illustrates another embodiment wherein the ultrasound imaging device UID is a bi-planar sonography probe defining an imaging region constituted by two sub-regions IR1 and IR2 which are substantially planar and lie in the yz and in the xz planes (imaging planes), respectively. The array of ultrasound transducers ATA is mounted so as to be rotatable around axes Ox and Oy. Electronic steering along the Oz' axis and tilting of the array ATA around the Ox and Oy axes allow displacing the focal point FP (which is actually a region of finite volume and with an elongate shape along Oz') within the two planar imaging regions IR1 and IR2.

According to yet another embodiment of the invention, not illustrated on the figures, the ultrasound imaging device UID is a three-dimensional matrix sonography probe defining a fully three-dimensional region, comprising infinitely many imaging planes, all including the Oz axis. The array of ultrasound transducers ATA is mounted so as to be rotatable around axes Ox and Oy. Electronic steering along the Oz' axis and tilting of the array ATA around the Ox and Oy axes allow displacing the focal point FP (which is actually a region of finite volume and with an elongate shape along Oz') within the three-dimensional imaging region.

As discussed above, the transducers are driven by a suitable electronic circuit ESG to generate ultrasonic waves. One possible driving circuit ESG is a pulsed power amplifier generating a time-delayed signal on each annular transducer. In particular embodiments of the invention, a set of sinusoid periods at a central frequency ranging from 100 kHz to 4 MHz, preferably from 500 kHz to 1 MHz, is applied to the transducers. This set of sinusoid periods called a burst is repeated at a regular frequency known as the Pulse Repetition Frequency (PRF) ranging from 0.01 to 1000 Hz. In this invention the length of a burst ranges from 1 µs up to 100 ms. In shock-wave—based applications, such as lithotripsy or histotripsy, the amplitude of the generated ultrasound waves should be sufficient to induce cavitation in biological tissues at the focal point. This means that the peak positive pressure generated at the focal point should be of at least 10 MPa and preferably of at least 50 MPa and the peak negative pressure should be of at least −5 MPa and preferably of at least −10 MPa.

The inventive device lends itself to a variety of medical applications. In cardiology, it allows cutting cardiac valve chords to treat mitral regurgitation, softening cardiac valves to treat valvular stenosis, creating intra-cardiac communications, etc. It is also suitable for non-cardiac applications, i.e. kidney stones, vascular calcifications, ablation of tumors. It is particularly suited to non-invasive applications, but can also be used invasively, e.g. being applied to the pericardium following sternotomy. It could also be used for the ultrasonic sonoporation or drug delivery of therapeutic agents in the heart for the controlled drug treatment of cardiac diseases.

The invention claimed is:

1. An ultrasound imaging and therapy device for performing non-invasive cardiac treatments, the ultrasound imaging and therapy device comprising:
an array of concentric annular ultrasound transducers, and
an ultrasound imaging device situated inside an innermost transducer of said plurality of concentric annular ultrasound transducers,
wherein the ultrasound imaging and therapy device further comprises a mechanical linkage allowing a tilting movement of the array of concentric annular ultrasound transducers with respect to the ultrasound imaging device and in that the ultrasound imaging device extends beyond the foremost point of the array of concentric annular ultrasound transducers, in an axial direction, by a length comprised between 10 and 100 mm;
whereby the ultrasound imaging device can be kept stationary and in direct or indirect contact with a patient's skin while the array of concentric annular ultrasound transducers is tilted so as to move a focal point of ultrasound waves generated by the concentric annular ultrasound transducers within an imaging region of said ultrasound imaging device;
wherein an indirect contact corresponds to a contact mediated by a layer of an ultrasound-conducting medium of less than 5 mm thick.

2. The ultrasound imaging and therapy device according to claim 1, wherein said mechanical linkage is adapted for allowing a rotational degree of freedom of the array of concentric annular ultrasound transducers with respect to the ultrasound imaging device around a single rotational axis perpendicular to an imaging plane of the ultrasound imaging device.

3. The ultrasound imaging and therapy device according to claim 1, wherein said ultrasound imaging device defines at least two mutually perpendicular imaging planes, and wherein said mechanical linkage is adapted for allowing a rotational degree of freedom of the array of concentric annular ultrasound transducers with respect to the ultrasound imaging device around two perpendicular rotational axes each perpendicular to a respective one of said imaging planes.

4. The ultrasound imaging and therapy device according to claim 3, or wherein said or each said rotational axis passes through a central point of the array of concentric annular ultrasound transducers.

5. The ultrasound imaging and therapy device according to claim 1, wherein the array of concentric annular ultrasound transducers has a concave shape.

6. The ultrasound imaging and therapy device according to claim 1, further comprising an electronic signal generator configured for driving said concentric annular ultrasound transducers with independent time delays so as to emit focused ultrasound waves with an adjustable focal length.

7. The ultrasound imaging and therapy device according to claim 6, wherein said electronic signal generator is configured for driving said concentric annular ultrasound transducers so as to emit said focused ultrasound waves with a focal point situated an axis perpendicular to the concentric annular ultrasound transducers and passing through a common center of said transducers, and for varying a position of said focal point along said axis.

8. The ultrasound imaging and therapy device according to claim 6, wherein said electronic signal generator and said concentric annular ultrasound transducers are configured for generating said focused ultrasound waves at an intensity level sufficient to generate, at the focal point, a peak positive pressure of at least 10 MPa and preferably of at least 50 MPa.

9. The ultrasound imaging and therapy device according to claim 6, wherein said electronic signal generator and said concentric annular ultrasound transducers are configured for generating said focused ultrasound waves at an intensity level sufficient to generate, at the focal point, a positive pressure comprised between 3 MPa and 10 MPa for HIFU therapy applications or ultrasonic drug delivery.

10. The ultrasound imaging and therapy device according to claim 6, further comprising an actuating system of said mechanical linkage.

11. The ultrasound imaging and therapy device according to claim 10, further comprising a controller configured for driving said electronic signal generator and said actuating system so as to steer the focal point of said focused ultrasound waves along a two- or three-dimensional path.

12. The ultrasound imaging and therapy device according to claim 11, wherein said controller is further configured for cooperating with said ultrasound imaging device so as to direct the focal point of said focused ultrasound waves onto an imaged anatomical target of a patient.

13. The ultrasound imaging and therapy device according to claim 11, wherein said controller is further configured for receiving image data provided by the imaging device, for processing said image data to extract information related to the treatment and for using said information to adapt automatically the intensity level of the focused ultrasound waves.

14. The ultrasound imaging and therapy device according to claim 13, wherein said information related to the treatment includes information on a cavitation activity.

15. The ultrasound imaging and therapy device according to claim 10, wherein said controller is further configured for receiving image data provided by the imaging device, for processing said image data to monitor in real-time the position of the therapeutic focus and for stopping the treatment if the focus is outside of a predefined target region.

* * * * *